United States Patent [19]

David-Comte et al.

[11] Patent Number: 5,498,716
[45] Date of Patent: Mar. 12, 1996

[54] 2-AMINO NAPHTHYRIDINE DERIVATIVE, ITS PREPARATION AND ITS USE

[75] Inventors: Marie-Thërèse David-Comte, Chevilly-Larue; Gérard Roussel, Soisy-sur-Seine, both of France

[73] Assignee: Rhone-Poulenc Rorer S.A., Antony, France

[21] Appl. No.: 181,641

[22] Filed: Jan. 12, 1994

[51] Int. Cl.[6] ................................................. C07D 471/04
[52] U.S. Cl. ....................................................... 546/122
[58] Field of Search ................................................. 546/122

[56] References Cited

U.S. PATENT DOCUMENTS 4,960,779  10/1990  Bourzat et al. .......................... 514/300
5,273,978  12/1993  Goto et al. ............................... 514/278

*Primary Examiner*—Bernard Dentz
*Attorney, Agent, or Firm*—Raymond S. Parker, III; Martin F. Savitzky; James A. Nicholson

[57] ABSTRACT

The present invention relates to a novel 2-aminonaphthyridine compounds that are useful in preparing a 2-isoindolinyl napthyridine compound that exhibits remarkable anxiolytic, hypnotic, anticonvulsant, antiepileptic and muscle-relaxant properties. The invention is also directed to the optical isomers of the 2-amino naphthyridine compounds and salts thereof, their preparation and the use of the 2-amino napthyridine compounds for preparing the 2-isoindolinyl napthyridine compound.

16 Claims, No Drawings

2-AMINO NAPHTHYRIDINE DERIVATIVE, ITS PREPARATION AND ITS USE

FIELD OF THE INVENTION

The present invention is directed to 2-amino napthyridine compounds useful for preparing a 2-isoindolinyl napthyridine compound that exhibits remarkable anxiolytic, hypnotic, anticonvulsant, antiepileptic and muscle-relaxant properties.

RECENT DEVELOPMENTS

The 2-isoindolinyl napthyridine compound of formula

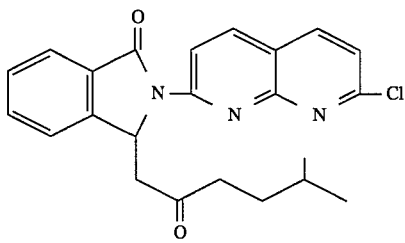

and analogous products which exhibit remarkable anxiolytic, hypnotic, anticonvulsant, antiepileptic and muscle-relaxant properties are the subject of U.S. Pat. No. 4,960,779. It has been shown that, in the 2-isoindolinyl napthyridine compound, the active entity or eutomer is the dextrorotatory (+) isomer.

According to U.S. Pat. No. 4,960,779, the separation of the optical isomers of the 2-isoindolinyl napthyridine compound may be carried out by chiral phase chromatography. However, the industrial application of this process is not always convenient to implement.

The object of the present invention is directed to novel compounds that are useful in preparing the 2-isoindolinyl napthyridine compound.

SUMMARY OF THE INVENTION

The present invention relates to novel 2-aminonaphthyridine compounds that are useful in preparing the 2-isoindolinyl napthyridine compound. The invention is also directed to the optical isomers of the 2-amino napthyridine compounds and salts thereof, their preparation and the use of the 2-amino napthyridine compounds for preparing the 2-isoindolinyl napthyridine compound.

DETAILED DESCRIPTION OF THE INVENTION

The present invention relates to the new 2-aminonaphthyridine derivative of formula (I):

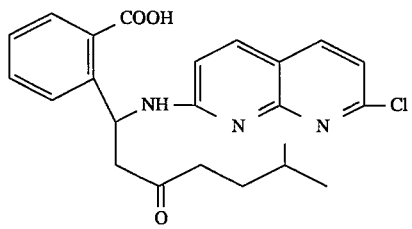

its preparation and its use for the preparation of the optical isomers of the product of formula (II):

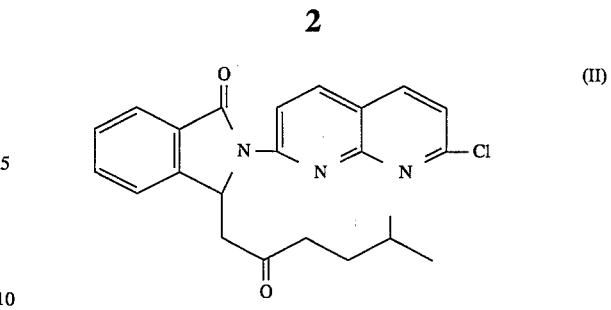

It has now been found, this being the subject of the present invention, that the product of formula (I), which has an asymmetric carbon atom and acidic and basic functional groups, is particularly advantageous for the preparation of the dextrorotatory isomer of the product of formula (II) by formation of a salt with a chiral base followed by the cyclization of the dextrorotatory isomer of the product of formula (I) to the dextrorotatory isomer of the product of formula (II).

According to the present invention, the product of formula (I) may be obtained by opening of the pyrrolinone ring of a racemic product of formula (II'):

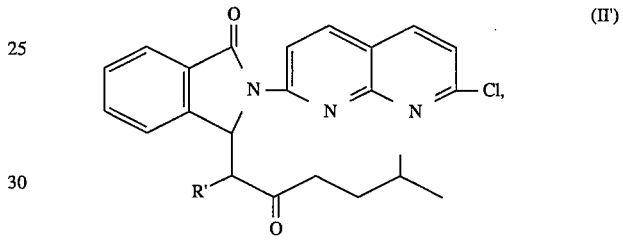

wherein R' is H or HOCO—, in basic medium.

Generally, the opening of the pyrrolinone ring is carried out by means of an inorganic base at a temperature of between 0° and 50° C. and, preferably, of between 0° and 30° C.

Generally, the process is carried out by stirring an aqueous-organic solution of the product of formula (II) in the presence of an excess of inorganic base chosen from the hydroxides and the carbonates or bicarbonates of alkali or alkaline-earth metals. It is particularly advantageous to use sodium hydroxide as inorganic base and to work in a water-pyridine mixture. It is also possible to carry out the reaction by using a water-dioxane mixture as solvent.

According to the invention, the new product of formula (I) may also be obtained by action of a base on the product of formula (III):

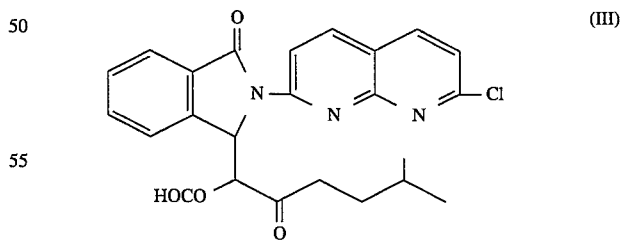

Generally, at least two equivalents of the inorganic base chosen, preferably, from sodium hydroxide, potassium hydroxide, sodium carbonate or potassium carbonate are used while working in water or in an aqueous-organic medium at a temperature of between 0° and 50° C., preferably between 0° and 30° C. A pyridine-water mixture is preferably used as aqueous-organic medium.

The product of formula (III) may be obtained by hydrolysis in acid medium of a product of general formula (IV):

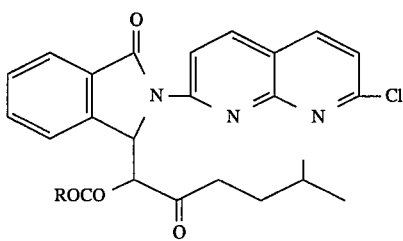

(IV)

in which R represents an alkyl radical containing 1 to 10 carbon atoms in a straight or branched chain.

Generally, the hydrolysis is carried out by means of a strong inorganic acid such as concentrated sulphuric acid while working at a temperature of between 0° and 50° C., preferably approximately 20° C.

The products of formulae (III) and (IV) may be obtained under the conditions described in American U.S. Pat. No. 4,960,779.

The new product of formula (I) may be purified by known methods such as by successive extractions in acidic and basic medium.

The new product of formula (I) may be converted to an addition salt with acids (hydrochloric, methanesulphonic, oxalic, maleic, fumaric acids) or to a salt with inorganic (sodium hydroxide, potassium hydroxide) or organic bases.

In order to prepare the eutomer of the product of formula (II), it is particularly advantageous to carry out, in succession, the following operations:

1) formation of a salt with a chiral base or a chiral acid;
2) precipitation of one of the optical isomers;
3) release of the dextrorotatory optical isomer of the product of formula (I), either from the precipitated salt or from the filtration mother liquors of the precipitated salt after optional formation of another salt with an appropriate chiral base or an appropriate chiral acid; and then
4) cyclization of the dextrorotatory optical isomer of the product of formula (I) to the dextrorotatory isomer of the product of formula (II) under nonracemising conditions.

It is thus possible to form a salt of the racemic product of formula (I) with (+)-ephedrine while working in an appropriate organic solvent such as ethanol. The salt of the dextrorotatory product of formula (I) and of (+)-ephedrine precipitates. The dextrorotatory isomer of the product of formula (I), which is displaced from its salt by means of a strong acid such as hydrochloric acid, is cyclized to the eutomer of the product of formula (II) by means of thionyl chloride while working optionally in the presence of a condensation agent such as imidazole or pyridine in an organic solvent such as methylene chloride.

It is not necessary to separate the dextrorotatory isomer of the product of formula (I) prior to the cyclization to the dextrorotatory product of formula (II).

It is also possible to prepare a salt of the product of formula (I) with cinchonine in an appropriate solvent such as ethanol, in which the salt is insoluble. The salt of the laevorotatory product of formula (I) with cinchonine precipitates. After being displaced from its cinchonine salt, the dextrorotatory isomer of the product of formula (I), which is found mainly in the filtration mother liquors of the laevorotatory salt, is converted into an insoluble salt with cinchonidine and more particularly a salt of the pure dextrorotatory isomer. The dextrorotatory isomer of the product of formula (I), which is displaced from its cinchonidine salt, is cyclized to the eutomer of the product of formula (II) under the conditions described previously.

The dextrorotatory isomer of the product of formula (I) is cyclized to the eutomer of the product of formula (II) by means of thionyl chloride, optionally in the presence of a condensing agent such as imidazole or pyridine in an organic solvent such as methylene chloride.

It is not necessary to separate the dextrorotatory isomer of the product of formula (I) prior to the cyclization to the dextrorotatory product of formula (II).

The following examples illustrate the present invention.

EXAMPLE 1

1400 cm$^3$ of dioxane and 20 g of (±)-2-(7-chloro-1,8-naphthyridin- 2-yl)-3-(5-methyl-2-oxohexyl)-1-isoindolinone are introduced, at a temperature of approximately 20° C., into a stirred, 2 liter reactor. 244 cm$^3$ of an N aqueous solution of sodium hydroxide are added over 5 minutes. The mixture is left to react for 4 days at a temperature below 30° C.

The dioxane is removed by distillation under reduced pressure (40 mm of mercury; 5.3 kPa) at a temperature below 30° C. 100 cm$^3$ of distilled water are added during the distillation.

An insoluble product is removed by filtration at 20° C. This product is washed with 3 times 50 cm$^3$ of distilled water and is removed. The combined aqueous phases are acidified by addition, over 3 hours, of 48 cm$^3$ of 5N hydrochloric acid at a temperature of 20° C. The pH of the suspension is then approximately 3.5.

After filtering the suspension, the precipitate is washed with 6 times 100 cm$^3$ of distilled water and is then dried under reduced pressure (15 mm of mercury; 2.0 kPa) at 60° C. for 16 hours.

14.3 g of (±)-2-{1-[(7-chloro-1,8-naphthyridin-2-yl)amino]-6-methyl-3-oxoheptyl}benzoic acid are thus obtained in the form of a white product whose retention time is 4.8 minutes by high performance liquid chromatography using a column 25 cm long and 0.46 cm in diameter with "Lichrospher O.D.S. 5 μm" as the stationary phase and a mixture of 200 cm$^3$ of pH 3, 25 mM phosphate buffer, 560 cm$^3$ of acetonitrile and 240 cm$^3$ of methanol, at a flow rate of 0.8 cm$^3$/minute, as the mobile phase.

(±)-2-(7-Chloro-1,8-naphthyridin-2-yl)-3-(5-methyl-2-oxohexyl)-1-isoindolinone can be prepared according to the method described in American U.S. Pat. No. 4,960,779.

EXAMPLE 2

20 g of (±)-2-(7-chloro-1,8-naphthyridin-2-yl)-3-(5-methyl- 2-oxohexyl)-1-isoindolinone, 400 cm$^3$ of pyridine and 60 cm$^3$ of a 2N aqueous sodium hydroxide solution are introduced, at a temperature of approximately 20° C., into a stirred, 1 liter reactor. The mixture is left to react for 23 hours and the pyridine is then distilled under reduced pressure (15 mm of mercury; 2.0 kPa) at a temperature below 20° C. 500 cm$^3$ of distilled water are added. An insoluble material is separated by filtration. The aqueous phase is acidified to pH=3.8 by addition of 40 cm$^3$ of 4N hydrochloric acid. The suspension is filtered, the precipitate is washed with 5 times 140 cm$^3$ of distilled water and then dried for 16 hours under reduced pressure (15 mm of mercury; 2.0 kPa) at 60° C.

19.2 g of (±)-2-{1-[(7-chloro-1,8-naphthyridin-2-yl)amino]-6-methyl-3-oxoheptyl}benzoic acid are thus obtained in the form of a white product whose retention time by high performance liquid chromatography is 4.8 minutes under the conditions described in Example 1.

EXAMPLE 3

A suspension of 30 mg of (±)-2-[2-(7-chloro-1,8-naphthyridin- 2-yl)-3-oxo-1-isoindolinyl]-6-methyl-3-oxoheptanoic acid in 4.7 cm$^3$ of distilled water and 1.32 cm$^3$ of a 0.1N aqueous sodium hydroxide solution is stirred at a temperature of approximately 20° C. for 72 hours. An insoluble product is removed by filtration and the filtrate is acidified to a pH=2 by addition of a 0.1N aqueous hydrochloric acid solution. The precipitate obtained is separated by filtration, washed with water and dried in air. 10 mg of (±)-2-{1-[ (7-chloro-1,8-naphthyridin-2-yl)amino]-6-methyl-3-oxoheptyl}benzoic acid are thus obtained whose characteristics are identical to those of the product of Example 1.

[2-(7-Chloro-1,8-naphthyridin-2-yl)-3-oxoheptanoic acid can be prepared in the following manner:

A solution of 23 g of ethyl 2-[2-(7-chloro-1,8-naphthyridin- 2-yl)-3-oxo-1-isoindolinyl]-6-methyl-3-oxoheptanoate in 235 cm$^3$ of 98% sulphuric acid is stirred for 20 hours at a temperature of approximately 20° C. and is then poured into 1.5 kg of ice. The precipitate obtained is separated by filtration, washed with water to a pH=6 and dried in air. The solid obtained is taken up in 3.8 liters of distilled water and 480 cm$^3$ of a 0.1N aqueous sodium hydroxide solution. The insoluble product is separated by filtration, the filtrate is acidified to a pH=3 by addition of a 0.1N aqueous hydrochloric acid solution. The precipitate obtained is separated by filtration, washed with distilled water and then with isopropyl ether and dried at 20° C. under reduced pressure (0.07 kPa). 9.2 g of (±)-2-[2-(7-chloro-1,8-naphthyridin-2-yl)-3-oxo-1-isoindolinyl]-6-methyl-3-oxoheptanoic acid, melting at 176° C., are thus obtained.

Ethyl 2-[2-(7-chloro-1,8-naphthyridin-2-yl)-3-oxo-1-isoindolinyl] -6-methyl-3-oxoheptanoate can be obtained by the method described in American U.S. Pat. No. 4,960,779.

EXAMPLE 4

1) 1450 cm$^3$ of 95% (v/v) ethanol, 100 g of cinchonine and 145 g of (±)-2-{1-[(7-chloro-1,8-naphthyridin-2-yl)amino]-6-methyl-3-oxoheptyl}benzoic acid are introduced into a stirred, 2 liter reactor. The suspension is heated to 40° C. and then cooled, over 3 hours 30 minutes, to 10° C. The suspension obtained is filtered. The precipitate is washed with 2 times 50 cm$^3$ of ethanol at 10° C. and then dried at 60° C. for 16 hours under reduced pressure (15 mm of mercury; 2.0 kPa). 99.3 g of the salt of cinchonine and of 2-{1-[(7-chloro-1,8-naphthyridin-2-yl) amino]-6-methyl-3-oxoheptyl}benzoic acid are thus obtained in the form of a white product whose characteristics are the following;

optical rotation: $[\alpha]^{20}_D$=+192.6° (c=1; methylene chloride)

enantiomeric purity: 98.5%.

250 cm$^3$ of N-methylpyrrolidone and 50 g of the salt obtained previously are introduced into a stirred, 2 liter reactor. 90 cm$^3$ of N hydrochloric acid are added, over 30 minutes, while maintaining the temperature at 20° C. The mixture is left for 1 hour at this temperature and then 660 cm$^3$ of distilled water are added over 1 hour. The suspension obtained is filtered. The precipitate is washed with 5 times 100 cm$^3$ of water and then dried at 60° C. for 16 hours under reduced pressure (15 mm of mercury; 2.0 kPa).

28.6 g of (−)-2-{1-[(7-chloro-1,8-naphthyridin-2-yl)amino]-6-methyl-3-oxoheptyl}benzoic acid are thus obtained in the form of a white product whose characteristics are the following:

optical rotation: $[\alpha]^{20}_D$=−227.4° (c=1; methylene chloride)

enantiomeric purity: 99.6%.

400 cm$^3$ of methylene chloride, 20 g of the product obtained previously and 21.8 g of imidazole are introduced at a temperature of 20° C., into a stirred, 1 liter reactor. 7 cm$^3$ of thionyl chloride are added, over 10 minutes, using a syringe. The suspension is heated at reflux for 30 minutes, is then cooled to 20° C. and washed with 2 times 200 cm$^3$ of distilled water. The washed solution is concentrated to half its volume and then 450 cm$^3$ of absolute ethanol are added. Distillation at atmospheric pressure is continued until the temperature of the vapours is 78° C. 1 g of decolorizing charcoal is added and the mixture is then held for 1 hour at 70° C. The suspension is filtered. The precipitate is washed with 50 cm$^3$ of ethanol at 75° C. The filtrate and the wash are combined. After cooling over 2 hours to 15° C., the suspension is filtered. The precipitate is washed with 3 times 35 cm$^3$ of ethanol and then dried at 60° C. for 16 hours under reduced pressure (15 mm of mercury; 2.0 kPa).

16.7 g of (−)-2-(7-chloro-1,8-naphthyridin-yl)-3-(5-methyl-2-oxohexyl)-1-isoindolinone are thus obtained in the form of a fluffy white product whose characteristics are the following:

optical rotation: $[\alpha]^{20}_D$=−132° (c=1; methylene chloride)

enantiomeric purity: 100%.

2) 1274.3 g of ethanolic liquors (corresponding to the filtrate of the cinchonine salt obtained previously with addition of the ethanol wash) are introduced into a 2 liter reactor. 260 cm$^3$ of an N aqueous hydrochloric acid solution are added at 20° C. After stirring for 15 minutes, 650 cm$^3$ of distilled water are added. The solution is concentrated under reduced pressure (25 mm of mercury; 3.3 kPa) at a temperature below 30° C. to remove the ethanol. The suspension is then filtered. The precipitate is washed with 6 times 100 cm$^3$ of water and then dried at 60° C. for 16 hours under reduced pressure (15 mm of mercury; 2.0 kPa).

79.6 g of a white product mostly consisting of the dextrorotatory isomer of 2-{1-[(7-chloro-1,8-naphthyridin-2-yl)amino]-6-methyl-3-oxoheptyl}benzoic acid are thus obtained, whose characteristics are the following:

optical rotation: $[\alpha]^{20}_D$=+160° (c=1; methylene chloride)

enantiomeric purity: 73.2%.

78.5 g of the product obtained previously, 54.3 g of cinchonidine and 700 cm$^3$ of 95% (v/v) ethanol are introduced into a 1 liter reactor. The solution is heated to reflux and then cooled over 3 hours to a temperature of 10° C. A product crystallizes. The suspension is filtered. The precipitate is washed with 2 times 50 cm$^3$ of 95% ethanol and then dried at 60° C. for 16 hours under reduced pressure (15 mm of mercury; 2.0 kPa).

92.8 g of the cinchonidine salt of (+)-2-{1-[(7-chloro-1, 8-naphthyridin- 2-yl)amino]-6-methyl-3-oxoheptyl}benzoic acid are thus obtained in the form of a white product whose characteristics are the following:

optical rotation: $[\alpha]^{20}_D$=−137.7° (c=1; methylene chloride)

enantiomeric purity: 100%.

50 g of the cinchonidine salt obtained previously are dissolved in 250 cm$^3$ of N-methylpyrrolidone in a 1 liter reactor. 90 cm$^3$ of N hydrochloric acid are added, over 30 minutes, while maintaining the temperature below 20° C.

After stirring for 15 minutes at 20° C., 600 cm³ of distilled water are added over 1 hour. The suspension obtained is filtered. The precipitate obtained is washed with 5 times 100 cm³ of distilled water and then dried at 60° C. for 16 hours under reduced pressure (15 mm of mercury; 2.0 kPa).

29.7 g of (+)-2-{1-[(7-chloro-1,8-naphthyridin-2-yl)amino]-6-methyl-3oxoheptyl}benzoic acid are thus obtained in the form of a white product whose characteristics are the following:

optical rotation: $[\alpha]^{20}_D = 222.8°$ (c=1; methylene chloride)

enantiomeric purity: 100%.

20 g of the dextrorotatory acid obtained previously and 21.8 g of imidazole are dissolved in 400 cm³ of methylene chloride in a 1 liter reactor. 7 cm³ of thionyl chloride are introduced, using a syringe, at a temperature of 20° C.. The suspension is heated at reflux for 30 minutes and is then cooled to 20° C. and is then washed 2 times with 200 cm³ of distilled water. The solution is concentrated, at atmospheric pressure, to half its volume and then 450 cm³ of absolute ethanol are added. The distillation of the methylene chloride is continued until the temperature of the vapour reaches 78° C. 1 g of decolorizing charcoal is then added and the mixture is then left for one hour at 78° C. The suspension is filtered. The precipitate is washed with 50 cm³ of absolute ethanol at 75° C. The filtrate and the washes are combined and then cooled to 15° C. over 2 hours. The suspension is filtered. The precipitate is washed with 3 times 35 cm³ of absolute ethanol at 15° C. and then dried at 60° C. for 16 hours under reduced pressure (15 mm of mercury; 2.0 kPa). 16.8 g of (+)-2-(7-chloro-1,8-naphthyridinyl)-3-(5-methyl-2-oxohexyl) 1-isoindolinone are thus obtained in the form of a fluffy white product whose characteristics are the following:

optical rotation: $[\alpha]^{20}_D = +132°$ (c=1; methylene chloride)

enantiomeric purity: 98.8%.

EXAMPLE 5

250 g of (±)-2-{1-[(7-chloro-1,8-naphthyridin-2-yl)amino]-6-methyl-3-oxoheptyl}benzoic acid, 97 g of (+)-ephedrine and 875 cm³ of 95% (v/v) ethanol are introduced, at a temperature of approximately 20° C., into a 2 liter reactor. After dissolving the suspension at 40° C., the reaction mixture is cooled to approximately 2° C. The precipitate obtained is separated by filtration, washed with 2 times 125 cm³ of 95% (v/v) ethanol at 2° C. and then dried for 16 hours at 60° C. under reduced pressure (15 mm of mercury; 2.0 kPa). 156.6 g of the salt of (+)-ephedrine and 2-{1-[(7-chloro-1,8-naphthyridin- 2-yl)amino]-6-methyl-3-oxoheptyl}benzoic acid are thus obtained in the form of a white product whose characteristics are the following:

optical rotation: $[\alpha]^{20}_D = -64°$ (c=1; methylene chloride)

enantiomeric purity: 100%.

2.75 g of the salt obtained previously and 5 cm³ of N-methylpyrrolidone are introduced into a 50 cm³ round bottom flask. 1.2 cm³ of concentrated hydrochloric acid and then, over 10 minutes, 15 cm³ of distilled water are added while maintaining the temperature at 20° C. The suspension obtained is filtered. The precipitate is washed with 5 times 10 cm³ of distilled water and then dried for 16 hours at 60° C. under reduced pressure (15 mm of mercury; 2.0kPa).

1.97 g of 2-{1-[(7-chloro-1,8-naphthyridin- 2-yl)amino]-6-methyl-3oxoheptyl}benzoic acid are thus obtained in the form of a white product whose characteristics are the following:

optical rotation: $[\alpha]^{20}_D = +222.8°$ (c=1; methylene chloride)

enantiomeric purity: 100%.

The product thus obtained is cyclized to (+)-2-(7-chloro-1,8-naphthyridin- 2-yl)-3-(5-methyl-2-oxohexyl)-1-isoindolinone under the conditions described previously in Example 4.

EXAMPLE 6

118.3 g of the salt of (+)-ephedrine and (±)-2-{1-[(7-chloro-1,8-naphthyridin-2-yl)amino]-6-methyl-3-oxoheptyl}benzoic acid and 1700 cm³ of methylene chloride are introduced into a 2.5 liter reactor. The organic solution is washed, at 20° C., with 400 cm³ of a 0.5N aqueous hydrochloric acid solution and then with 400 cm³ of distilled water. The organic phase is dehydrated by azeotropic distillation at 20° C. under reduced pressure (250 mm of mercury; 33.3 kPa). The volume of the organic phase is adjusted to 1700 cm³ by addition of dry methylene chloride, 95.2 g of imidazole are then added and then, over 10 minutes, 25 cm³ of thionyl chloride. The suspension is heated at 40° C. for 30 minutes, then cooled to 20° C. and washed with 2 times 700 cm³ of distilled water. The methylene chloride is removed by distillation at atmospheric pressure while adding, to keep the volume constant, 2500 cm³ of absolute ethanol. When the temperature of the vapour reaches 78° C., the distillation is halted and 4 g of decolorizing charcoal in suspension in 20 cm³ of absolute ethanol are then added. The mixture is left for 30 minutes at 78° C. and then filtered while hot. The decolorizing charcoal is rinsed with 200 cm³ of ethanol at 77° C. The wash and the filtrate are combined and then cooled, at a rate of 20° C./hour, to a temperature of 10° C. The suspension is filtered. The precipitate is washed with 3 times 140 cm³ of absolute ethanol at 10° C. and then dried at 60° C. for 16 hours under reduced pressure (15 mm of mercury; 2.0 kPa). The slightly yellow product obtained (68.9 g) is recrystallized from 1400 cm³ of ethanol at reflux. After cooling to 10° C., the suspension is filtered. The precipitate is washed with 3 times 100 cm³ of absolute ethanol at 10° C. and then dried at 60° C. for 16 hours under reduced pressure (15 mm of mercury; 2.0 kPa). 65.1 g of (+)-2-(7-chloro-1,8-naphthyridin- 2-yl)-3-(5-methyl-2-oxohexyl)-1-isoindolinone are thus obtained in the form of a fluffy white product whose characteristics are the following:

optical rotation: $[\alpha]^{20}_D = +132°$ (c=1; methylene chloride)

enantiomeric purity: 100%.

We claim:

1. A 2-amino naphthyridine compound of formula (I):

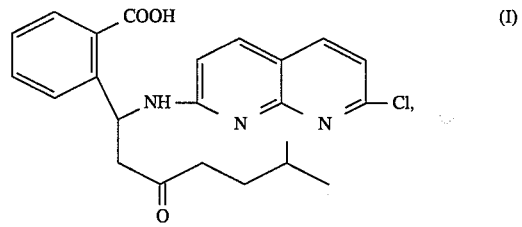

optical isomers of the 2-amino naphthyridine compound or a salt thereof.

2. Process for preparing the 2-amino naphthyridine compound of claim 1, comprising reacting a base with the compound of formula (II'):

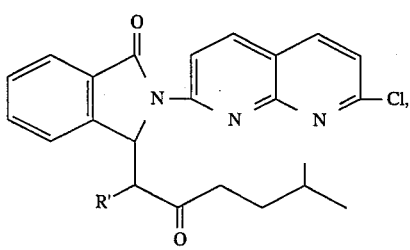

wherein R' is H or HOCO—, isolating the 2-amino naphthyridine compound, optionally separating the optical isomers of the 2-amino naphthyridine compound, and optionally converting the 2-amino naphthyridine compound or its optical isomers to a salt thereof.

3. Process according to claim 1, wherein R' is H.

4. Process according to claim 1, wherein R' is HOCO—.

5. Process for preparing of the dextrorotatory isomer of the 2-amino naphthyridine compound of formula (I) according to claim 1, comprising reacting (+)-ephedrine with the racemic 2-amino naphthyridine compound of formula (I) according to claim 1 to precipitate a (+)-ephedrine salt of the 2-amino naphthyridine compound which is enriched in the dextrorotatory isomer, isolating the salt and releasing the dextrorotatory isomer.

6. Process according to claim 5, wherein the reacting takes place in an organic solvent such as ethanol.

7. Process according to claim 5, wherein the releasing is carried out by means of a strong acid such as hydrochloric acid.

8. Process for preparing of the dextrorotatory isomer of the 2-amino naphthyridine compound of formula (I) according to claim 1, comprising reacting cinchonine in an organic solvent with the racemic 2-amino naphthyridine compound of formula (I) according to claim 1 to precipitate a cinchonine salt of the 2-amino naphthyridine compound which is enriched in the laevorotatory isomer, separating the salt from the solvent containing a cinchonine salt of the 2-amino naphthyridine compound which is enriched in the dextrorotatory isomer, displacing the cinchonine from the cinchonine salt of the 2-amino naphthyridine compound which is enriched in the dextrorotatory isomer, reacting the 2-amino naphthyridine compound which is enriched in the dextrorotatory isomer in an organic solvent with cinchonidine to precipitate a cinchonidine salt of the 2-amino naphthyridine compound enriched in the dextrorotatory isomer, and releasing the 2-amino naphthyridine compound enriched in the dextrorotatory isomer from its cinchonidine salt.

9. Process according to claim 8, wherein the organic solvent is ethanol to precipitate the cinchonine salt of the 2-amino naphthyridine compound enriched in the laevorotatory isomer.

10. Process according to claim 8, wherein the displacing is carried out by means of a strong acid.

11. Process according to claim 8, wherein the organic solvent is ethanol to precipitate the cinchonidine salt of the 2-amino naphthyridine compound enriched in the dextrorotatory isomer.

12. Process according to claim 8, wherein the releasing is carried out by means of a strong acid.

13. Process for preparing of the dextrorotatory isomer of formula (II),

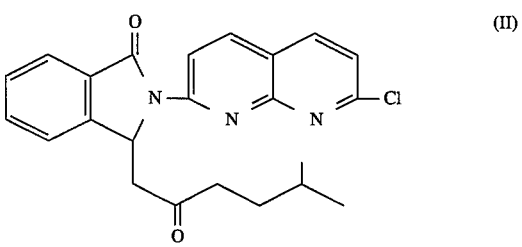

comprising cyclyzing the dextrorotatory isomer of formula (I):

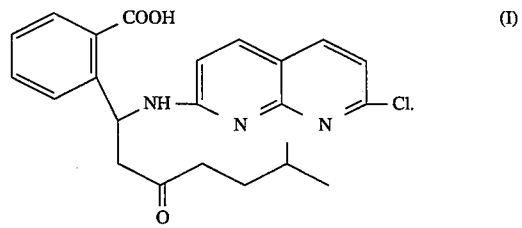

14. Process according to claim 13, wherein the cyclyzing is carried out by means of thionyl chloride in the presence of a condensation agent.

15. Process according to claim 14, wherein the condensation agent is imidazole or pyridine.

16. Process according to claim 13, wherein the cyclyzing is carried out in an organic solvent.

* * * * *